(12) United States Patent
Chiang

(10) Patent No.: US 11,154,307 B2
(45) Date of Patent: Oct. 26, 2021

(54) SURGICAL DRILL AND METHOD OF CONTROLLING THE AUTOMATIC STOP THEREOF

(71) Applicant: ORION BIOTECH INC., Taipei (TW)

(72) Inventor: Ming-Fu Chiang, Taipei (TW)

(73) Assignee: ORION BIOTECH INC., Taipei (TW)

( * ) Notice: Subject to any disclaimer, the term of this patent is extended or adjusted under 35 U.S.C. 154(b) by 339 days.

(21) Appl. No.: 16/435,499

(22) Filed: Jun. 9, 2019

(65) Prior Publication Data

US 2019/0321054 A1 Oct. 24, 2019

Related U.S. Application Data

(62) Division of application No. 15/173,593, filed on Jun. 3, 2016, now abandoned.

(51) Int. Cl.
*A61B 17/16* (2006.01)
*A61B 90/00* (2016.01)
*A61B 17/00* (2006.01)

(52) U.S. Cl.
CPC .......... *A61B 17/1626* (2013.01); *A61B 90/03* (2016.02); *A61B 2017/00022* (2013.01); *A61B 2090/031* (2016.02); *A61B 2090/062* (2016.02)

(58) Field of Classification Search
CPC .................................................. A61B 17/1626
See application file for complete search history.

(56) References Cited

U.S. PATENT DOCUMENTS

| | | | | |
|---|---|---|---|---|
| 5,599,142 A | * | 2/1997 | Fujimoto | B23Q 15/12 408/10 |
| 6,786,683 B2 | * | 9/2004 | Schaer | B23B 49/006 408/16 |
| 8,511,945 B2 | * | 8/2013 | Apkarian | A61B 17/1626 408/1 R |
| 10,245,043 B2 | * | 4/2019 | Xie | A61B 90/03 |
| 2004/0215395 A1 | * | 10/2004 | Strasser | B23B 49/006 702/9 |
| 2005/0116673 A1 | * | 6/2005 | Carl | A61B 17/1626 318/432 |
| 2005/0131415 A1 | * | 6/2005 | Hearn | A61B 17/8875 606/80 |

* cited by examiner

*Primary Examiner* — Andrew Yang
(74) *Attorney, Agent, or Firm* — Cheng-Ju Chiang

(57) ABSTRACT

A method of controlling automatic stop of a surgical drill 1) uses a smart module to receive instantaneous electrical signals of a driving device coupled to the surgical drill; 2) sets the length of a unit time, and sets the average of all instantaneous electrical signals received in a unit time as a reference electrical signal; and 3) compares the instantaneous electrical signal with the reference electrical signal. When the instantaneous electrical signal experiences a step drop with respect to the reference electrical signal, the smart module sends a stop command to the driving device to stop the operation of the driving device.

5 Claims, 6 Drawing Sheets

SURGICAL DRILL AND METHOD OF CONTROLLING THE AUTOMATIC STOP THEREOF

CROSS REFERENCE TO RELATED APPLICATIONS

The present application is a division of prior U.S. application Ser. No. 15/173,593 filed Jun. 3, 2016, entitled "SURGICAL DRILL AND METHOD OF CONTROLLING THE AUTOMATIC STOP THEREOF".

FIELD OF THE INVENTION

The present invention relates to the field of medical instruments, and more particularly to a surgical drill and a method of controlling the automatic stop of the surgical drill solar panel module.

BACKGROUND OF THE INVENTION

Surgical bone drills are mainly divided into manual drills and electrical drills. In the manual bone drill, the rotating speed, the drilling depth, and the start and end of the drill are controlled manually by a surgeon. The surgeon operates the bone drill based on experience and hand feel. At the moment of drilling through bone tissues, the bone drilling resistance drops significantly and the surgeon's hand may sense such drop significantly, but the surgeon is unable to stop the drilling operation instantaneously. Therefore, blood vessels, nerves, or fascia may be drilled and damaged easily, and the patient safety may be jeopardized.

On the other hand, the electrical bone drill steadily receives electromechanical torque from a mechanical structure to achieve an automatic rotating effect of a drill bit, so that the electrical bone drill has the advantages of reducing the force or load required for the surgeon's drilling operation and shortening the bone drilling time, but it still has the disadvantage that the surgeon is unable to feel the drop of bone drilling resistance through both hands and stop the bone drilling operation timely. If the surgeon cannot stop drilling bone tissues timely, the high-speed drill bit may damage blood vessels, nerves, muscles or fascia more seriously than the manual bone drill.

SUMMARY OF THE INVENTION

Therefore, it is a primary objective of the present invention to overcome the aforementioned drawbacks of the conventional electrical bone drill by providing a surgical drill capable of stopping its operation instantaneously while the surgical drill is drilling bone tissues as well as calculating the bone drilling depth of the surgical drill automatically.

To achieve the aforementioned and other objectives, the present invention provides a surgical drill, comprising: a drill bit, a driving device coupled to the drill bit, and a smart module electrically coupled to the driving device; when the surgical drill performs a bone drilling work, the smart module receives an instantaneous electrical signal of the driving device, and compares the instantaneous electrical signal with a reference electrical signal, and if the instantaneous electrical signal has a step drop with respect to the reference electrical signal, the smart module will send a stop command to the driving device to stop the operation of the driving device.

To achieve the aforementioned and other objectives, the present invention provides a method of controlling the automatic stop of a surgical drill, and the method is executed by a smart module electrically coupled to a driving device of the surgical drill. The method comprises the following steps:

Receive a plurality of instantaneous electrical signals of the driving device per second when the surgical drill executes a bone drilling work.

Set a plurality of consecutive seconds as a unit time, and use an average of all instantaneous electrical signals in the unit time as a reference electrical signal.

Compare the instantaneous electrical signal with the reference electrical signal.

When the instantaneous electrical signal has a step drop with respect to the reference electrical signal, stop the operation of the driving device and a stop command is sent to the driving device.

To achieve the aforementioned and other objectives, the present invention provides a method of controlling the automatic stop of a surgical drill and measuring a bone drilling depth, and the method is executed by a smart module electrically coupled to a driving device of the surgical drill and a non-contact distance measuring device electrically coupled to the smart module. The method comprises the following steps:

Receive a plurality of instantaneous electrical signals of the driving device per second when the surgical drill executes a bone drilling work.

Set a plurality of consecutive seconds as a unit time, and use an average of all instantaneous electrical signals in the unit time as a reference electrical signal.

Compare the instantaneous electrical signal with the reference electrical signal.

Send a stop command to the driving device to stop the operation of the driving device, when the instantaneous electrical signal has a step drop with respect to the reference electrical signal.

Send a first distance measuring command to the non-contact distance measuring device by the smart module when the surgical drill is started, and obtain a first distance (D1) from a light source emitting point to an outer side of a cortical layer by the non-contact distance measuring device, and receive the first distance by the smart module. Send a second distance measuring command to the non-contact distance measuring device by the smart module when the surgical drill is controlled to stop its operation by the smart module, and obtain a second distance (D2) from a light source emitting point to an outer side of the cortical layer, and receive the second distance (D2) by the smart module. Execute the operation of [D1–D2] by the smart module to obtain a bone drilling depth value, and displaying the bone drilling depth value on a display screen of the bone drilling depth measuring device.

The present invention has the following effects:

The surgical drill may be stopped immediately and automatically at the moment of drilling bone tissues by a drill bit. The automatic stop of the operation of the surgical drill alerts the surgeon that he has already drilled through the cortical layer already. The automatic stop also provides the safety effect of protecting the tissues, blood vessels, muscles, nerves and fascia behind the cortical layer and prevents them from being damaged by the surgical bone drill that drills through the cortical layer.

The smart module of the present invention is compatible with surgical drill of any model and specification without the need of changing the structure of the surgical drill or adding additional components or modules. The smart module of the present invention has the automatic stop function regardless of the model and specification of the surgical drill.

The smart module of the present invention allows the surgical drill to have the automatic stop function, while maintaining the external structure of the surgical drill without requiring extra components, and facilitates the overall disinfection of the surgical drill for aseptic packaging.

The surgical drill with the smart module in accordance with the present invention adopts the non-contact distance measuring device to achieve the function of calculating the bone drilling depth automatically while maintaining the external structure of the surgical drill without requiring any additional component and facilitates the overall disinfection of the surgical drill for aseptic packaging.

DESCRIPTION OF THE PREFERRED EMBODIMENTS

The objective of the invention, its structure, innovative features, and performance will become apparent in the following detailed description of the preferred embodiments with reference to the accompanying drawings.

Figure 1:
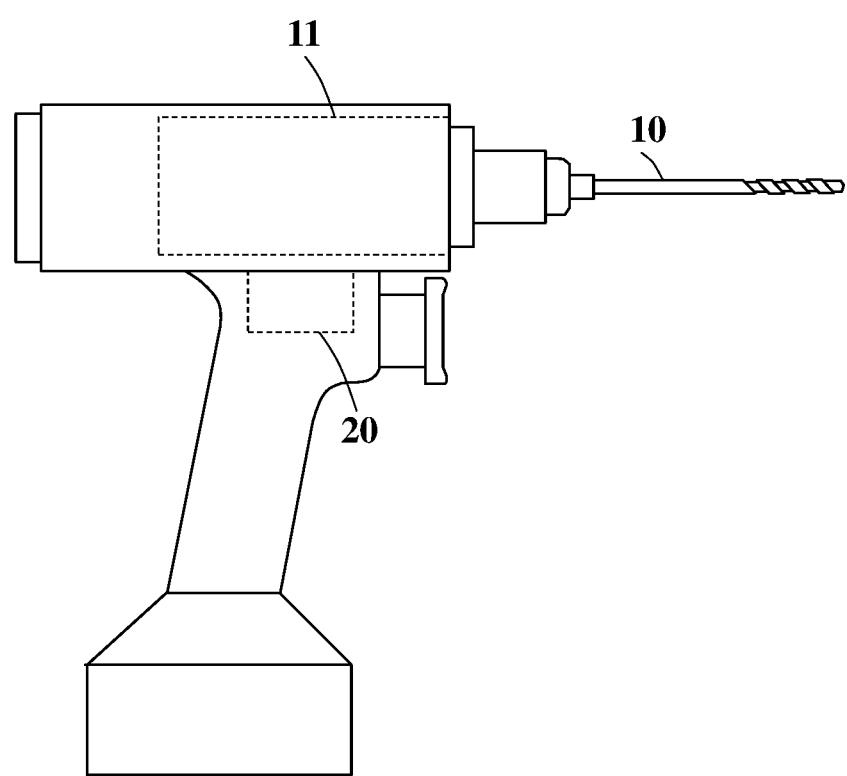
FIG. 1 is a schematic view of a surgical drill of the present invention.

With reference to FIG. 1 for a surgical drill of the present invention, the surgical drill comprises a drill bit 10, a driving device 11 connected and electrically coupled to the drill bit 10, and a smart module 20 electrically coupled to the driving device 11.

In a surgical drilling work, the smart module 20 continues monitoring and obtaining an instantaneous electrical signal, wherein the electrical signal is represented by one including, but not limited to, a voltage. The smart module 20 compares the instantaneous electrical signal with a reference electrical signal, and if the instantaneous electrical signal has a step drop with respect to the reference electrical signal, the smart module 20 will send a stop command to the driving device 11 to stop the operation of the driving device 11.

The reference electrical signal may be an absolute electrical signal or a sampling electrical signal. The absolute electrical signal is a built-in default value in the smart module 20. The sampling electrical signal is an average of all instantaneous electrical signals in a unit time during the surgical drilling work. The unit time includes a plurality of consecutive seconds, wherein the unit time may be fixed or rolling with the working time of the surgical drill. Assumed that consecutive four seconds are used as a unit time, and the fixed unit time constantly uses the [$N^{th}$ to $N+3^{th}$] seconds of the bone drilling work as the sampling time, wherein the sampling time remains constant. The unit time with the ascending unit time uses the $1^{st}$ to $4^{th}$ seconds, the second to $5^{th}$ seconds, the third to $6^{th}$ seconds (so on and so forth) as the sampling time of the bone drilling work, wherein the sampling time varies and ascends (or rolls) with the time of the bone drilling work.

Figure 2:
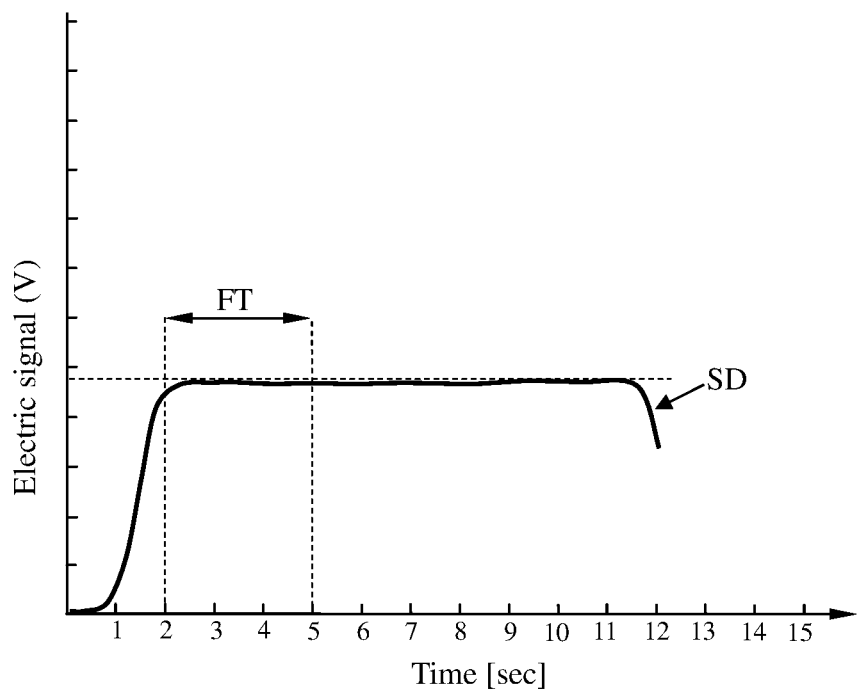
FIG. 2 is a schematic view showing the instantaneous electrical signal over a time domain, a sampling electrical signal (or a reference electrical signal) over a fixed time ("FT") and a step drop ("SD") in accordance with the present invention.
Figure 3:
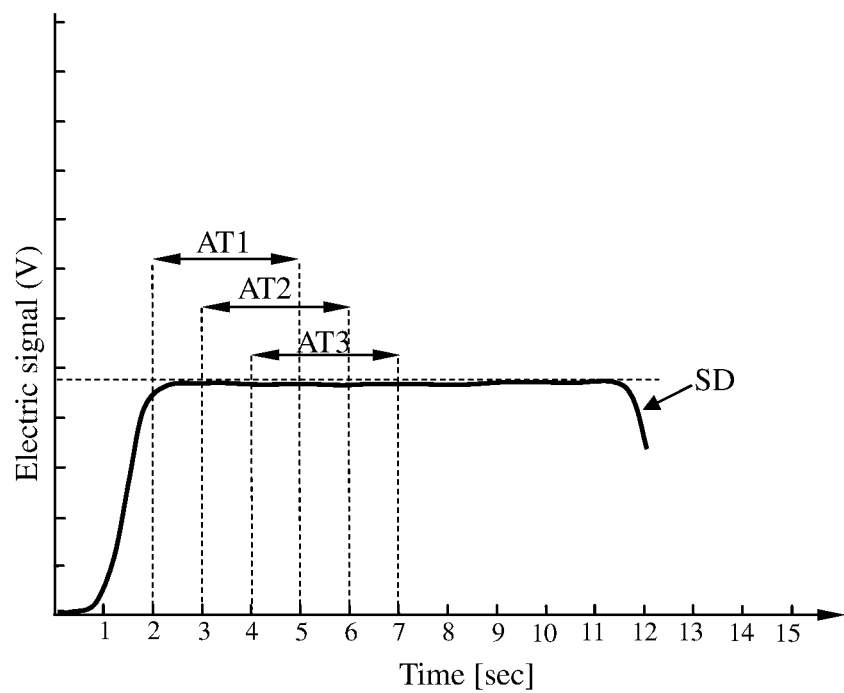
FIG. 3 is a schematic view showing ascending or rolling unit times in accordance with the present invention.
Figure 4:
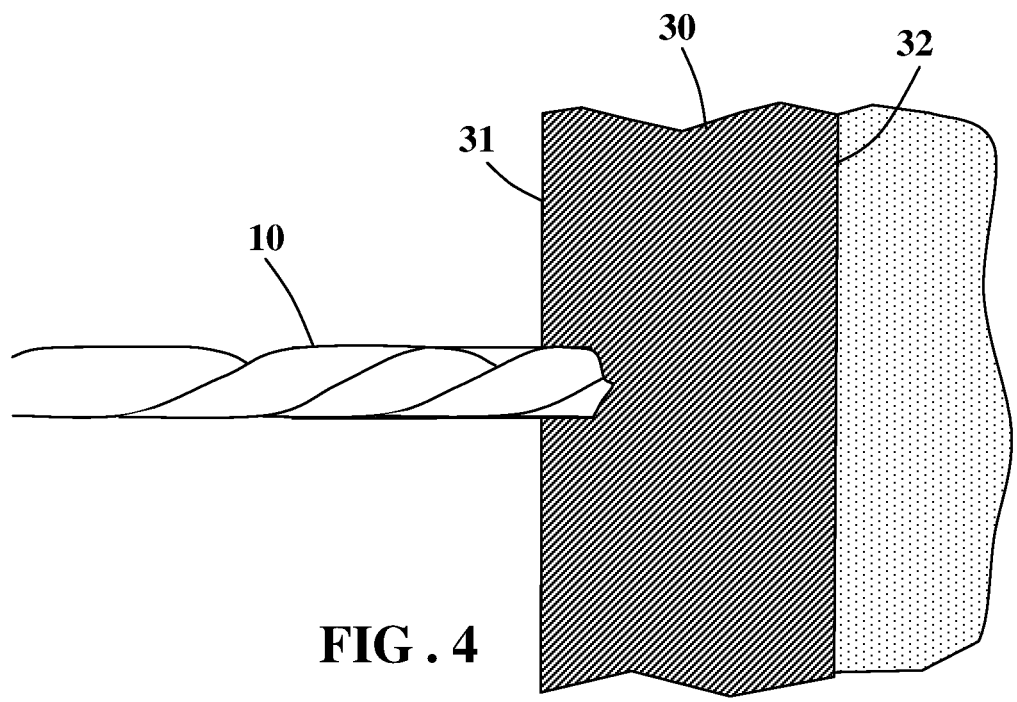
FIG. 4 is a first schematic view of a surgical drill executing a bone drilling work in accordance with the present invention.
Figure 5:
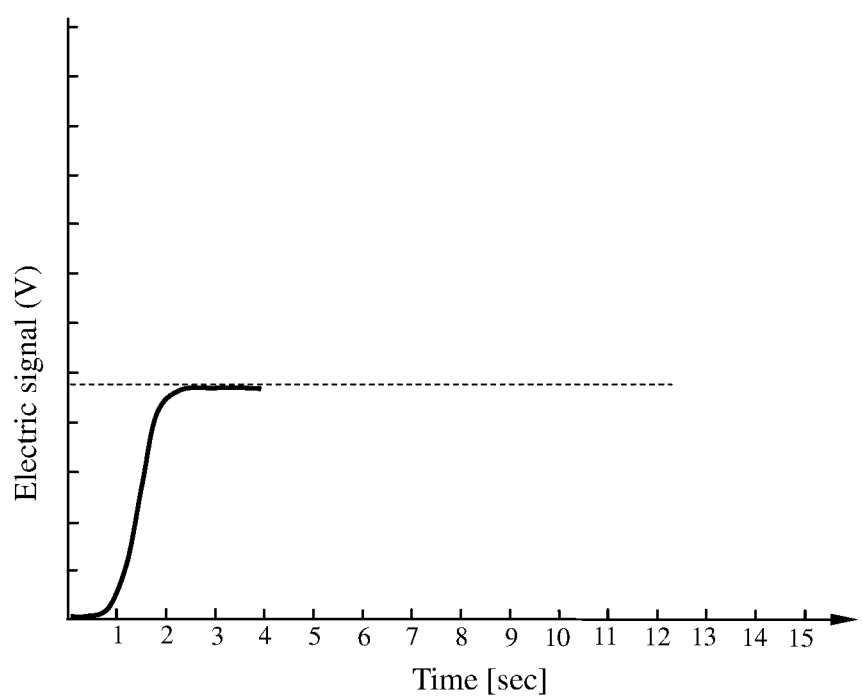
FIG. 5 is a schematic view showing the electrical signal over a time domain corresponding to FIG. 4.
Figure 6:
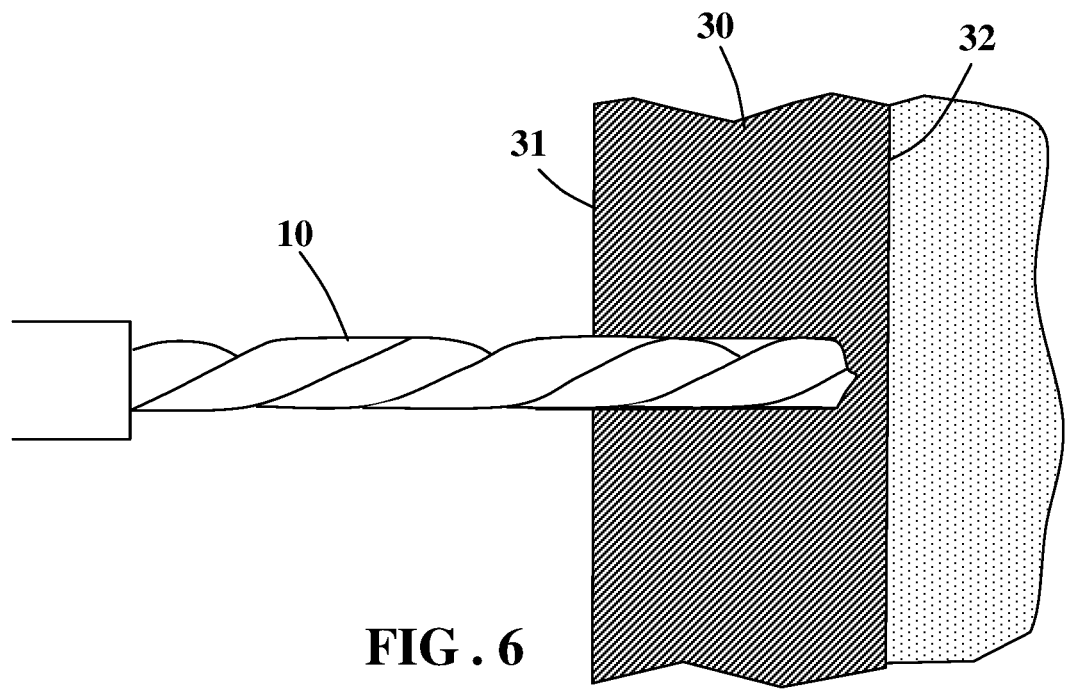
FIG. 6 is a second schematic view of a surgical drill executing a bone drilling work in accordance with the present invention.
Figure 7:
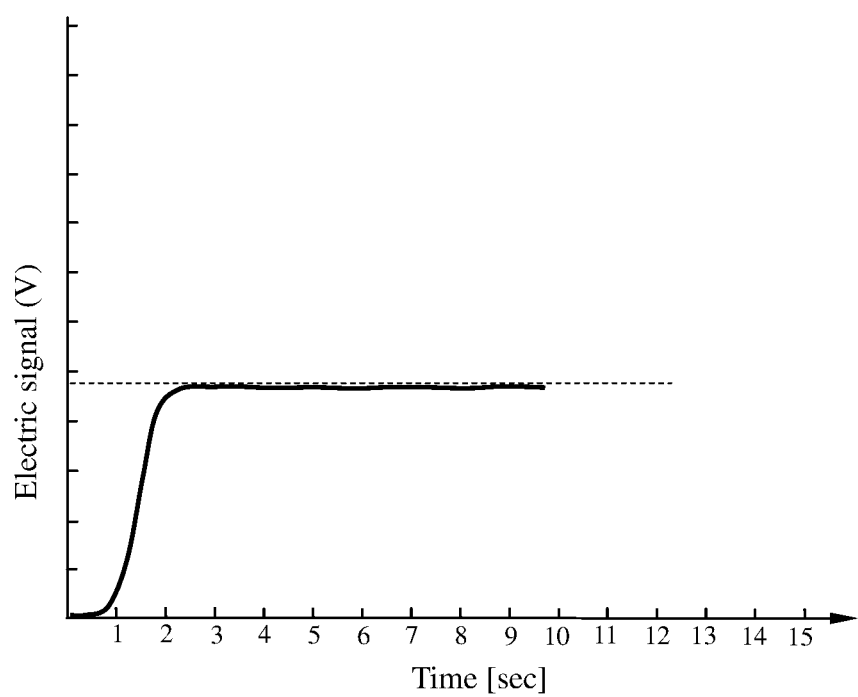
FIG. 7 is a schematic view of showing the electrical signal over a time domain corresponding to FIG. 6.

With reference to FIGS. 2 and 3 for the schematic views of using a time domain method to show an instantaneous electrical signal, a sampling electrical signal (or a reference electrical signal) and a step drop in accordance with the present invention, the x-axis represents the surgical drill working time (sec) and the y-axis represents the electrical signal (voltage) of the driving device of the surgical drill. During the surgical drilling work, the smart module 20 obtains the electrical signal per second and uses it as an instantaneous electrical signal, and the smart module 20 also obtains an average of instantaneous electrical signals in a unit time and uses it as a reference electrical signal. In FIG. 2, the reference electrical signal is generated in a fixed unit time. For example, consecutive four seconds are used as a unit time, and the second to fifth seconds are used as the fixed unit time (FT), and an average of all instantaneous electrical signals in the fixed unit time (FT) is used as a reference electrical signal as well as a reference for comparing the instantaneous electrical signal per second. In other words, the instantaneous electrical signals at the sixth second and thereafter are compared with the reference electrical signal at the second to fifth seconds (FT). With reference to FIG. 3 for the reference electrical signals generated at the unit time of ascending unit time (for example, consecutive four seconds are used as a unit time, and the surgical drill working time at the $2^{nd}$~$5^{th}$ seconds (AT1), the $3^{rd}$~6th seconds (AT2), the $4^{th}$~$7^{th}$ seconds (AT3), so on and so forth, are used as a unit time, wherein the unit time ascends or rolls with the bone drilling work. In other words, when the surgical drilling work is carried on to the sixth second, the average of the instantaneous electrical signals of (AT1) is used as a reference electrical signal of the sixth second. When the work is carried on to the seventh second, the average of the instantaneous electrical signals of AT2 is used as a reference electrical signal of the seventh second. When the work is carried on to the eighth second, the average of the instantaneous electrical signals of AT3 is used as a reference electrical signal of the eighth second, and so on and so forth. Preferably, the instantaneous electrical signal should be compared with the reference electrical signal that is happened closest to the unit time. In FIGS. 2 and 3, as the work is carried on with time, the smart module 20 constantly obtains the instantaneous electrical signals and compares them with the reference electrical signal until an electrical signal with a step drop shows up. In FIGS. 2 and 3, the step drop (SD) has a waveform with a steep drop. In other words, the instantaneous electrical signal drops drastically and shows a significant difference with the reference electrical signal.

Figure 8:
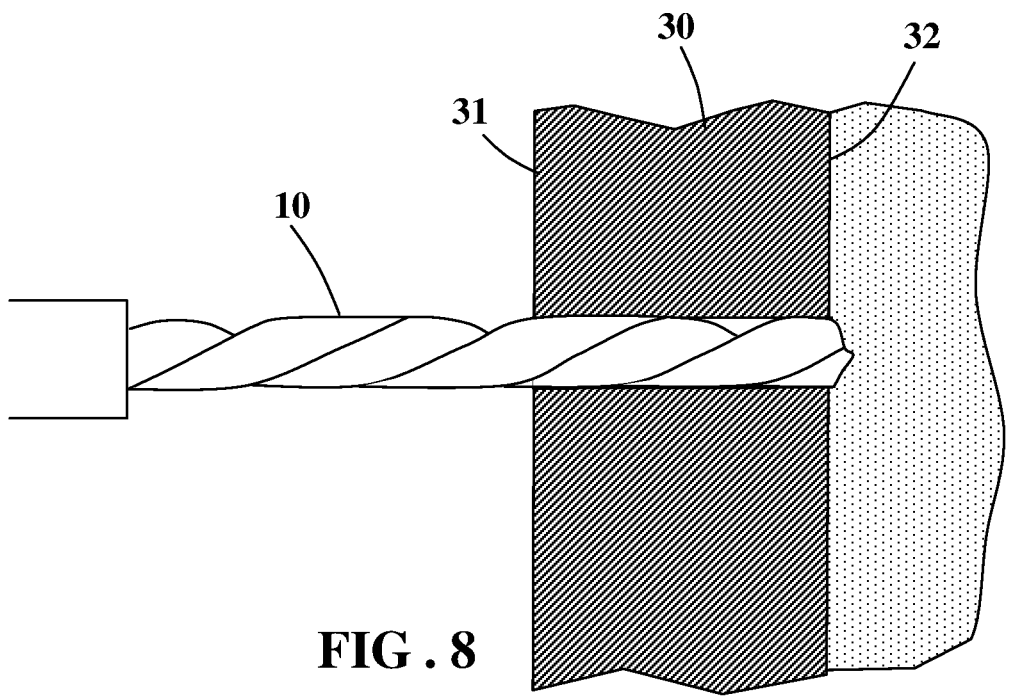
FIG. 8 is a third schematic view of a surgical drill executing a bone drilling work in accordance with the present invention.
Figure 9:
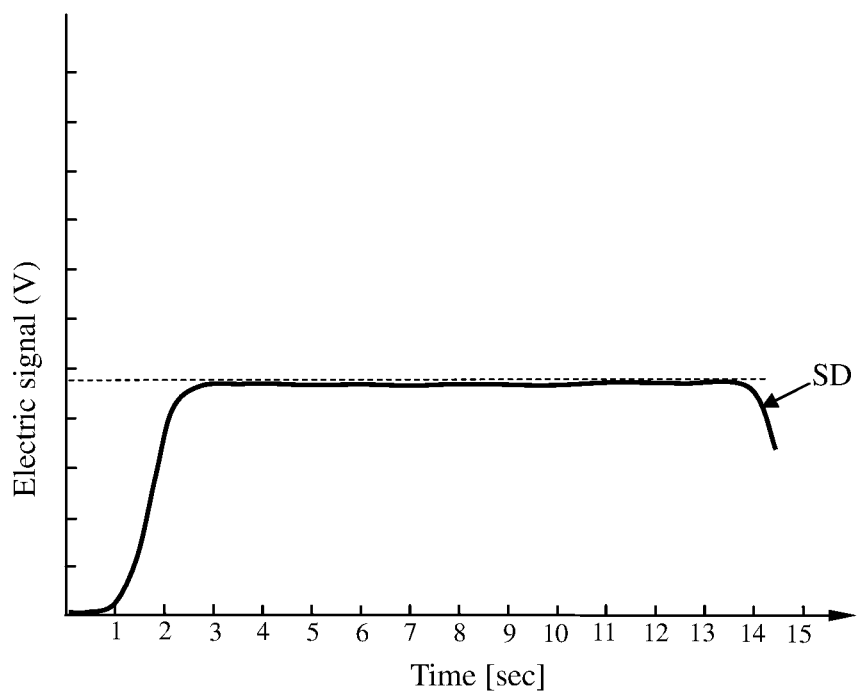
FIG. 9 is a schematic view showing the electrical signal over a time domain corresponding to FIG. 8.

With reference to FIGS. 4 to 9 for the bone drilling work executed by a surgical drill of the present invention, a drill bit 10 is provided for drilling from the outer side 31 to the inner side 32 of the cortical layer 30. In FIGS. 4 to 7, when the drill bit 10 has not drilled through the cortical layer 30, the rotating speed of the drill bit 10 is substantially constant, and the output voltage of the driving device 11 is also substantially constant, and the instantaneous electrical signal (voltage) obtained by the smart module 20 is substantially maintained at a standard level. The smart module 20 compares all obtained instantaneous electrical signals with the reference electrical signal. Since the instantaneous electrical signal and the reference electrical signal are maintained at a standard level, the smart module 20 will not output a stop command, and the driving device 11 of the surgical drill continues its operation. In FIGS. 8 and 9, when the tip of the drill bit 10 drills through the inner side 32 of the cortical layer 30, the rotating speed of the drill bit 10 increases drastically, and the current output of the driving device 11 increases, so that the voltage drops drastically, and the instantaneous electrical signal obtained by the smart module 20 has a step drop (SD) and shows a significant difference from the reference electrical signal, and the smart module 20 sends a stop command to the driving device 11 to stop the operation of the driving device 11. The automatic stop of the driving device 11 and the drill bit 10 reminds the surgeon that the drilling has passed through the cortical layer. The automatic stop also provides the safety effect of protecting the tissues, blood vessels, muscles, nerves and fascia behind the cortical layer and prevents them from being damaged by the surgical bone drill that drills through the cortical layer. Unless the surgeon turns on the power of the surgical drill again, the surgical drill will remain at the OFF status.

Figure 10:
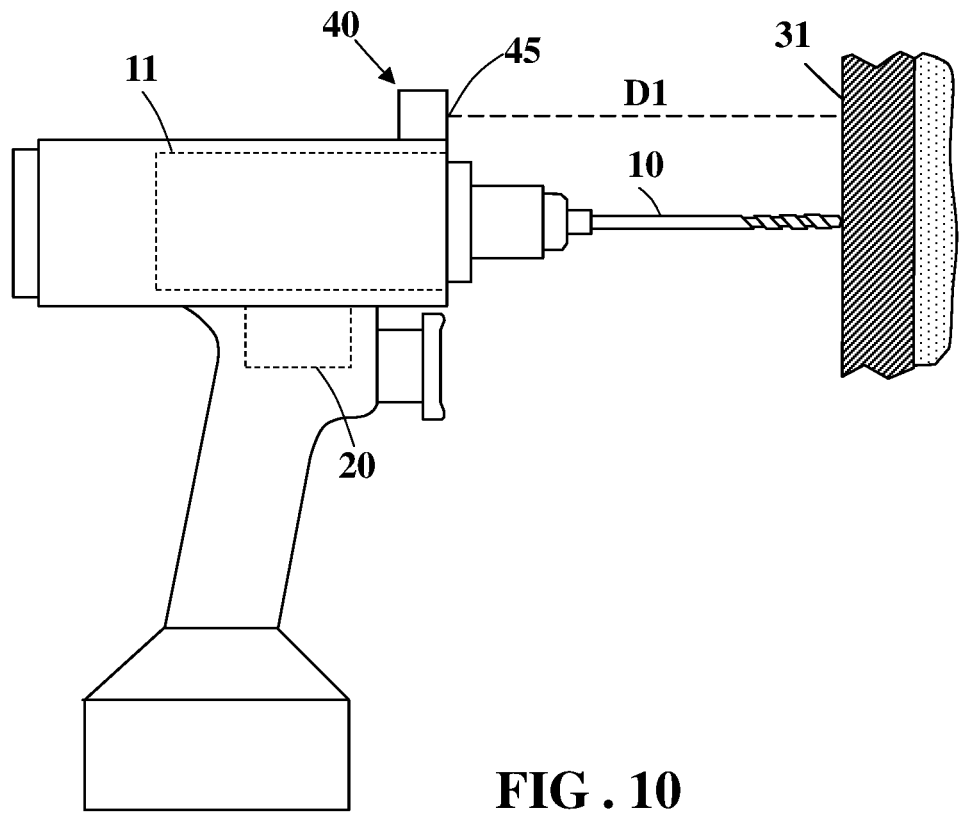
FIG. 10 is a schematic view of a surgical drill executing a bone drilling depth measurement at the start of a bone drilling work in accordance with the present invention.
Figure 11:
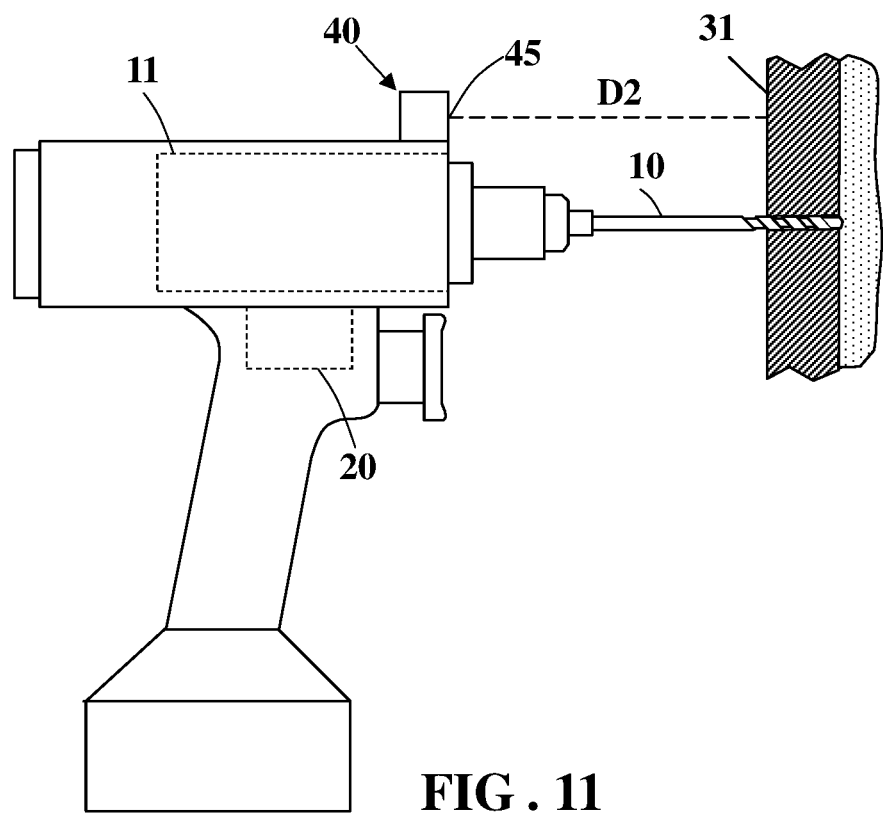
FIG. 11 is a schematic view of a surgical drill executing a bone drilling depth measurement after the drilling is stopped in accordance with the present invention.

In FIGS. 10 and 11, the surgical drill further comprises a measuring device 40 for measuring a bone drilling depth, wherein the measuring device 40 is installed on the surgical drill and electrically coupled to the smart module 20, and the measuring device 40 is a non-contact distance measuring device including but not limited to a lightwave distance measuring module, an infrared distance measuring module, and a laser distance measuring module. When the surgical drill is turned on, the smart module 20 sends a first distance measuring command to the device 40, and the device 40 obtains a first distance (D1) from a light source emitting point 45 to an outer side 31 of a cortical layer 30, and the smart module 20 receives the first distance (D1). When the surgical drill is controlled to stop its operation by the smart module 20, the smart module 20 sends a second distance measuring command to the device 40, and the device 40 obtains a second distance (D2) from the light source emitting point to the outer side 31 of the cortical layer 30, and the smart module 20 receives the second distance (D2). The smart module 20 executes the operation of [D1−D2] to obtain a bone drilling depth value, and the bone drilling depth value is displayed on a screen display 41 of the bone drilling depth measuring device 40.

What is claimed is:

1. A method of controlling automatic stop of a surgical drill, executed by a smart module electrically coupled to a driving device of the surgical drill, the method comprising the steps of:
   receiving a plurality of instantaneous electrical signals of the driving device per second when the surgical drill executes a bone drilling work;
   setting a plurality of consecutive seconds as a unit time, and setting an average of all instantaneous electrical signals in the unit time as a reference electrical signal;
   comparing the instantaneous electrical signal with the reference electrical signal; and
   when the instantaneous electrical signal has a step drop with respect to the reference electrical signal, sending a stop command to the driving device to stop operation of the driving device.

2. The method according to claim 1, wherein the unit time is a fixed time.

3. The method according to claim 1, wherein the unit time rolls with working time of the surgical drill.

4. The method according to claim 1, wherein the instantaneous electrical signal is compared with reference electrical signal that is happened closest to the unit time.

5. A method of controlling automatic stop of a surgical drill and measuring a bone drilling depth, executed by a smart module electrically coupled to a driving device of the surgical drill and a non-contact distance measuring device electrically coupled to the smart module, the method comprising the steps of:
   receiving a plurality of instantaneous electrical signals of the driving device per second when the surgical drill executes a bone drilling work;
   setting a plurality of consecutive seconds as a unit time, and setting an average of all instantaneous electrical signals in the unit time as a reference electrical signal;
   comparing the instantaneous electrical signal with the reference electrical signal;
   sending a stop command to the driving device to stop operation of the driving device, when the instantaneous electrical signal has a step drop with respect to the reference electrical signal;
   when the surgical drill is started, the smart module sending a first distance measuring command to the non-contact distance measuring device to obtain a first distance (D1) from a light source emitting point to an outer side of a cortical layer and send the first distance to the smart module;
   when the stop command is sent to stop operation of the driving device, the smart module sending a second distance measuring command to the non-contact distance measuring device to obtain a second distance (D2) from a light source emitting point to an outer side of the cortical layer and send the second distance (D2) to the smart module; and
   executing the operation of [D1−D2] by the smart module to obtain a bone drilling depth value, and displaying the bone drilling depth value on a display screen of the bone drilling depth measuring device.

* * * * *